United States Patent
Shoham

(10) Patent No.: US 11,890,451 B2
(45) Date of Patent: Feb. 6, 2024

(54) ANTI-FREE-FLOW VALVE

(71) Applicant: EITAN MEDICAL LTD., Netanya (IL)

(72) Inventor: Oriya Shoham, Yakir (IL)

(73) Assignee: EITAN MEDICAL LTD., Netanya (IL)

(*) Notice: Subject to any disclaimer, the term of this patent is extended or adjusted under 35 U.S.C. 154(b) by 224 days.

(21) Appl. No.: 17/433,377

(22) PCT Filed: Mar. 4, 2020

(86) PCT No.: PCT/IL2020/050249
§ 371 (c)(1),
(2) Date: Aug. 24, 2021

(87) PCT Pub. No.: WO2020/178827
PCT Pub. Date: Sep. 10, 2020

(65) Prior Publication Data
US 2022/0040405 A1    Feb. 10, 2022

Related U.S. Application Data

(60) Provisional application No. 62/814,053, filed on Mar. 5, 2019.

(51) Int. Cl.
*A61M 5/168*    (2006.01)
*A61M 5/145*    (2006.01)
*A61M 39/28*    (2006.01)

(52) U.S. Cl.
CPC ...... *A61M 5/16813* (2013.01); *A61M 5/1452* (2013.01); *A61M 5/16881* (2013.01);
(Continued)

(58) Field of Classification Search
CPC ......... A61M 2005/14506; A61M 2005/14573; A61M 2005/16863; A61M 2039/226;
(Continued)

(56) References Cited

U.S. PATENT DOCUMENTS 3,379,950 A    4/1968    Friedline
4,236,880 A    12/1980    Archibald
(Continued)

FOREIGN PATENT DOCUMENTS

CN    103727021    4/2014
EP    0182502    5/1986
(Continued)

OTHER PUBLICATIONS

An Office Action dated Sep. 30, 2019, which issued during the prosecution of U.S. Appl. No. 15/740,365.
(Continued)

*Primary Examiner* — Shefali D Patel
(74) *Attorney, Agent, or Firm* — The Roy Gross Law Firm, LLC; Roy Gross

(57) ABSTRACT

An apparatus for delivering a fluid to a subject through infusion tubing (22). The apparatus includes a tube cassette (20) for receiving the infusion tubing. The tube cassette has an anti-free-flow valve (26) configured to (i) occlude the infusion tubing, and (ii) be actuated by a force external to the tube cassette to terminate the occlusion of the infusion tubing. The tube cassette is configured to be removably coupled to a pump (24). The pump is configured to, as part of a pumping cycle for delivering the fluid to the subject, repeatedly (a) actuate the anti-free-flow valve to terminate the occlusion of the infusion tubing, and subsequently (b) release the anti-free-flow valve to occlude the infusion tubing. Other applications are also described.

13 Claims, 4 Drawing Sheets

(52) U.S. Cl.
CPC ........ *A61M 39/281* (2013.01); *A61M 39/284* (2013.01); *A61M 2005/16863* (2013.01); *A61M 2205/128* (2013.01)

(58) Field of Classification Search
CPC ........ A61M 2205/12; A61M 2205/128; A61M 39/22; A61M 39/26; A61M 39/28; A61M 39/281; A61M 39/284; A61M 5/14; A61M 5/142; A61M 5/14212; A61M 5/14216; A61M 5/1422; A61M 5/14228; A61M 5/145; A61M 5/1452; A61M 5/1454; A61M 5/14566; A61M 5/168; A61M 5/16804; A61M 5/16809; A61M 5/16813; A61M 5/16877; A61M 5/16881
See application file for complete search history.

(56) References Cited

U.S. PATENT DOCUMENTS

| | | | |
|---|---|---|---|
| 4,322,668 A | 3/1982 | Trussler et al. | |
| 4,391,600 A | 7/1983 | Archibald | |
| 4,650,469 A | 3/1987 | Berg et al. | |
| 5,018,945 A | 5/1991 | D'Silva | |
| 5,049,047 A | 9/1991 | Polaschegg et al. | |
| 5,096,385 A | 3/1992 | Georgi et al. | |
| 5,116,203 A | 5/1992 | Natwick et al. | |
| 5,340,951 A | 8/1994 | Hungerbuhler et al. | |
| 5,437,642 A | 8/1995 | Thill et al. | |
| 5,567,119 A | 10/1996 | Johnson | |
| 5,807,075 A | 9/1998 | Jacobsen et al. | |
| 5,807,322 A | 9/1998 | Lindsey et al. | |
| 5,843,035 A | 12/1998 | Bowman et al. | |
| 5,954,485 A | 9/1999 | Johnson et al. | |
| 6,312,227 B1 | 11/2001 | Davis | |
| 6,494,864 B1 | 12/2002 | Kerwin et al. | |
| 6,523,414 B1 | 2/2003 | Malmstrom et al. | |
| 6,531,708 B1 | 3/2003 | Malmstrom et al. | |
| 6,554,806 B2 | 4/2003 | Butterfield et al. | |
| 6,659,976 B2 | 12/2003 | Beck et al. | |
| 6,679,862 B2 | 1/2004 | Diaz et al. | |
| 6,702,779 B2 | 3/2004 | Connelly et al. | |
| 6,750,468 B2 | 6/2004 | Malmstrom et al. | |
| 6,852,094 B2 | 2/2005 | Beck et al. | |
| 6,889,556 B2 | 5/2005 | Steger | |
| 6,907,788 B2 | 6/2005 | Malmstrom et al. | |
| 6,908,452 B2 | 6/2005 | Diaz et al. | |
| 6,979,311 B2 | 12/2005 | Miles et al. | |
| 7,048,715 B2 | 5/2006 | Diaz et al. | |
| 7,059,840 B2 | 6/2006 | Corwin et al. | |
| 7,070,575 B2 | 7/2006 | Beck et al. | |
| 7,092,796 B2 | 8/2006 | Vanderveen | |
| 7,121,143 B2 | 10/2006 | Malmstrom et al. | |
| 7,163,381 B1 | 1/2007 | Barak | |
| 7,356,382 B2 | 4/2008 | Vanderveen | |
| 7,384,408 B2 | 6/2008 | Barak | |
| 7,497,842 B2 | 3/2009 | Diaz et al. | |
| 7,695,448 B2 | 4/2010 | Cassidy et al. | |
| 7,726,174 B2 | 6/2010 | Riley et al. | |
| 7,758,551 B2 | 7/2010 | Wiesner et al. | |
| 7,819,838 B2 | 10/2010 | Ziegler et al. | |
| 7,875,004 B2 | 1/2011 | Yodfat et al. | |
| 7,881,883 B2 | 2/2011 | Remde | |
| 7,892,199 B2 | 2/2011 | Mhatre et al. | |
| 7,896,197 B2 | 3/2011 | Furey et al. | |
| 7,921,718 B2 | 4/2011 | Malmstrom et al. | |
| 7,922,700 B2 | 4/2011 | Evans et al. | |
| 7,967,773 B2 | 6/2011 | Amborn et al. | |
| 7,981,082 B2 | 7/2011 | Wang et al. | |
| 8,025,654 B2 | 9/2011 | Barak | |
| 8,034,020 B2 | 10/2011 | Dewey | |
| 8,048,022 B2 | 11/2011 | Moy et al. | |
| 8,081,069 B2 | 12/2011 | Haueter et al. | |
| 8,105,269 B2 | 1/2012 | Zhou | |
| 8,142,400 B2 | 3/2012 | Rotem et al. | |
| 8,152,780 B2 | 4/2012 | Evans et al. | |
| 8,167,832 B2 | 5/2012 | Bowman et al. | |
| 8,182,461 B2 | 5/2012 | Pope et al. | |
| 8,197,235 B2 * | 6/2012 | Davis | F04B 43/04 417/474 |
| 8,225,639 B2 | 7/2012 | Riley et al. | |
| 8,232,484 B2 | 7/2012 | Hauck | |
| 8,286,505 B2 | 10/2012 | Wade | |
| 8,287,495 B2 | 10/2012 | Michaud et al. | |
| 8,298,184 B2 | 10/2012 | Diperna et al. | |
| 8,328,786 B2 | 12/2012 | Strickler et al. | |
| 8,343,111 B2 | 1/2013 | Beck et al. | |
| 8,361,021 B2 | 1/2013 | Wang et al. | |
| 8,378,837 B2 | 2/2013 | Wang et al. | |
| 8,394,051 B2 | 3/2013 | Geipel | |
| 8,419,676 B2 | 4/2013 | Evans et al. | |
| 8,448,523 B2 | 5/2013 | Richter | |
| 8,486,005 B2 | 7/2013 | Yodfat et al. | |
| 8,486,020 B2 | 7/2013 | Hills et al. | |
| 8,496,613 B2 | 7/2013 | Zhou | |
| 8,539,672 B2 | 9/2013 | Eggers et al. | |
| 8,567,235 B2 | 10/2013 | Bojan et al. | |
| 8,641,671 B2 | 2/2014 | Michaud et al. | |
| 8,657,778 B2 | 2/2014 | Ziegler et al. | |
| 8,690,014 B2 | 4/2014 | Haueter et al. | |
| 8,690,860 B2 | 4/2014 | Abal | |
| 8,733,178 B2 | 5/2014 | Bivans et al. | |
| 8,752,436 B2 | 6/2014 | Beck et al. | |
| 8,758,323 B2 | 6/2014 | Michaud et al. | |
| 8,771,227 B2 | 7/2014 | Connelly et al. | |
| 8,795,225 B2 | 8/2014 | Lewis et al. | |
| 8,808,230 B2 | 8/2014 | Rotstein | |
| 8,821,432 B2 | 9/2014 | Unverdorben | |
| 8,852,141 B2 | 10/2014 | Mhatre et al. | |
| 8,859,972 B2 | 10/2014 | Cummings et al. | |
| 8,876,787 B2 | 11/2014 | Beck et al. | |
| 8,900,213 B2 | 12/2014 | Pope et al. | |
| 8,926,561 B2 | 1/2015 | Verhoef et al. | |
| 8,943,894 B2 | 2/2015 | Geipel | |
| 8,945,064 B2 | 2/2015 | Gravesen et al. | |
| 8,961,453 B2 | 2/2015 | Bowman et al. | |
| 8,974,415 B2 | 3/2015 | Robert et al. | |
| 8,986,253 B2 | 3/2015 | Diperna | |
| 9,004,886 B2 | 4/2015 | Beck et al. | |
| 9,005,153 B2 | 4/2015 | Kopperschmidt et al. | |
| 9,017,296 B2 | 4/2015 | Beck et al. | |
| 9,033,923 B2 | 5/2015 | Hartman et al. | |
| 9,101,712 B2 | 8/2015 | Denis et al. | |
| 9,109,966 B2 | 8/2015 | Duits | |
| 9,132,230 B2 | 9/2015 | Blomquist | |
| 9,162,023 B2 | 10/2015 | Barnes et al. | |
| 9,173,998 B2 | 11/2015 | Rosinko et al. | |
| 9,211,377 B2 | 12/2015 | Diperna et al. | |
| 9,227,008 B2 | 1/2016 | Magnenat et al. | |
| 9,234,850 B2 | 1/2016 | Hammond et al. | |
| 9,248,230 B2 | 2/2016 | Geipel et al. | |
| 9,272,087 B2 | 3/2016 | Halbert et al. | |
| 9,285,324 B2 | 3/2016 | Leuenberger Jockel | |
| 9,308,323 B2 | 4/2016 | Adams | |
| 9,375,531 B1 | 6/2016 | Lee et al. | |
| 9,408,968 B2 | 8/2016 | Browne et al. | |
| 9,415,158 B2 | 8/2016 | Miller et al. | |
| 9,427,521 B2 | 8/2016 | Pope et al. | |
| 9,468,713 B2 | 10/2016 | Hoenninger, III et al. | |
| 9,474,854 B2 | 10/2016 | Mhatre et al. | |
| 9,480,793 B2 | 11/2016 | Mhatre et al. | |
| 9,480,794 B2 | 11/2016 | Keith et al. | |
| 9,545,478 B2 | 1/2017 | Abal | |
| 9,561,323 B2 | 2/2017 | Plahey et al. | |
| 9,603,998 B2 | 3/2017 | Geipel et al. | |
| 9,610,404 B2 | 4/2017 | Rotstein | |
| 9,642,777 B2 | 5/2017 | Lewis et al. | |
| 9,662,437 B2 | 5/2017 | Moosai | |
| 9,675,756 B2 | 6/2017 | Kamen et al. | |
| 9,677,555 B2 | 6/2017 | Kamen et al. | |
| 9,682,192 B2 | 6/2017 | Marsh et al. | |
| 9,683,562 B2 | 6/2017 | Davis et al. | |
| 9,717,849 B2 | 8/2017 | Mhatre et al. | |
| 9,757,517 B2 | 9/2017 | Eberhard | |

(56) References Cited

U.S. PATENT DOCUMENTS

| | | |
|---|---|---|
| 9,770,552 B2 | 9/2017 | Hartman et al. |
| 9,775,947 B2 | 10/2017 | Keith et al. |
| 9,789,251 B2 | 10/2017 | Robert et al. |
| 9,839,744 B2 | 12/2017 | Muto et al. |
| 9,879,668 B2 | 1/2018 | Yavorsky et al. |
| 9,901,676 B2 | 2/2018 | Mijers et al. |
| 9,932,977 B2 | 4/2018 | Bresina et al. |
| 9,937,290 B2 | 4/2018 | Connelly et al. |
| 9,937,291 B2 | 4/2018 | Eberhard |
| 9,958,344 B2 | 5/2018 | Burkhard |
| 9,962,486 B2 | 5/2018 | Rosinko et al. |
| 9,987,424 B2 | 6/2018 | Kim |
| 9,995,642 B2 | 6/2018 | Shimoyama et al. |
| 10,004,847 B2 | 6/2018 | Wander et al. |
| 10,006,453 B2 | 6/2018 | Girard et al. |
| 10,022,494 B2 | 7/2018 | Shimizu |
| 10,022,495 B2 | 7/2018 | Halbert et al. |
| 10,022,496 B2 | 7/2018 | Geipel et al. |
| 10,046,112 B2 | 8/2018 | Oruklu et al. |
| 10,080,836 B2 | 9/2018 | Juretich et al. |
| 10,092,697 B2 | 10/2018 | Nessel et al. |
| 10,112,009 B2 | 10/2018 | Dudar et al. |
| 10,151,646 B2 | 12/2018 | Heo et al. |
| 10,539,453 B2 | 1/2020 | Hauck |
| 11,213,460 B2 | 1/2022 | O'Keefe et al. |
| 2003/0141468 A1 | 7/2003 | Malmstrom et al. |
| 2005/0107923 A1 | 5/2005 | Vanderveen |
| 2006/0173412 A1 | 8/2006 | Susi |
| 2006/0189926 A1 | 8/2006 | Hall et al. |
| 2006/0206054 A1 | 9/2006 | Shekalim |
| 2007/0123781 A1 | 5/2007 | Callahan et al. |
| 2007/0179435 A1 | 8/2007 | Braig et al. |
| 2008/0283296 A1 | 11/2008 | Zamora et al. |
| 2009/0221964 A1 | 9/2009 | Rotem et al. |
| 2009/0240201 A1 | 9/2009 | Rotem et al. |
| 2009/0293588 A1 | 12/2009 | Riley et al. |
| 2010/0106082 A1 | 4/2010 | Zhou |
| 2010/0114001 A1 | 5/2010 | O'Mahony |
| 2010/0212407 A1 | 8/2010 | Stringham et al. |
| 2010/0280446 A1 | 11/2010 | Kalpin |
| 2011/0087165 A1 | 4/2011 | Amborn et al. |
| 2011/0152772 A1 | 6/2011 | Rotem et al. |
| 2011/0190606 A1 | 8/2011 | Gable et al. |
| 2012/0205312 A1 | 8/2012 | Hogard |
| 2012/0238949 A1 | 9/2012 | Kalpin |
| 2012/0330574 A1 | 12/2012 | Ruiter et al. |
| 2013/0035659 A1 | 2/2013 | Hungerford et al. |
| 2013/0226129 A1 | 8/2013 | Unverdorben |
| 2013/0336814 A1 | 12/2013 | Kamen et al. |
| 2014/0066850 A1 | 3/2014 | Robert et al. |
| 2014/0119954 A1 | 5/2014 | Schweitzer et al. |
| 2014/0121639 A1 | 5/2014 | Lowery et al. |
| 2014/0228755 A1 | 8/2014 | Darrah et al. |
| 2015/0238689 A1 | 8/2015 | Shimizu |
| 2015/0367120 A1 | 12/2015 | Kusters et al. |
| 2018/0140770 A1 | 5/2018 | Hetchler et al. |
| 2018/0200456 A1 | 7/2018 | Eitan et al. |
| 2018/0318505 A1 | 11/2018 | Eitan et al. |
| 2020/0085695 A1 | 3/2020 | O'Keefe et al. |
| 2020/0282138 A1 | 9/2020 | Eitan et al. |
| 2021/0178062 A1 | 6/2021 | Eitan |
| 2021/0212903 A1 | 7/2021 | O'Keefe et al. |
| 2021/0353507 A1 | 11/2021 | O'Keefe et al. |

FOREIGN PATENT DOCUMENTS

| | | | |
|---|---|---|---|
| EP | 1381843 | 3/2009 | |
| EP | 2040056 | 9/2010 | |
| EP | 1381889 | 3/2016 | |
| EP | 2570826 | 8/2016 | |
| EP | 3834862 | 6/2021 | |
| FR | 2553151 | 4/1985 | |
| GB | 2150644 | 7/1985 | |
| WO | WO-9421918 A1 * | 9/1994 | ............ F04B 43/082 |
| WO | 02/068018 | 9/2002 | |
| WO | 2012/126744 | 9/2012 | |
| WO | 2019/155453 | 8/2019 | |
| WO | 2020060996 A1 | 3/2020 | |
| WO | 2020/178824 | 9/2020 | |
| WO | 2021146374 A1 | 7/2021 | |

OTHER PUBLICATIONS

European Search Report dated Jun. 21, 2019 which issued during the prosecution of European Application No. 16817348.2.

An International Search Report and a Written Opinion both dated Aug. 5, 2018, which issued during the prosecution of Applicant's PCT/IL2018/050409.

An Office Action dated Jun. 22, 2020, which issued during the prosecution of U.S. Appl. No. 15/740,365.

European Search Report dated Jun. 4, 2020, which issued during the prosecution of Applicant's European App No. 20160966.6.

An International Search Report and a Written Opinion both dated Jun. 9, 2020, which issued during the prosecution of Applicant's PCT/IL2020/050246.

European Search Report dated May 12, 2021 which issued during the prosecution of Applicant's European App No. 20212979.7.

U.S. Appl. No. 62/814,053, filed Mar. 5, 2019.

European Search Report dated Oct. 8, 2021 which issued during the prosecution of Applicant's European App No. 18905766.4.

Notice of Allowance dated Aug. 4, 2021, which issued during the prosecution of U.S. Appl. No. 16/808,652.

An International Search Report and a Written Opinion both dated May 15, 2020, which issued during the prosecution of Applicant's PCT/IL2020/050249.

* cited by examiner

ANTI-FREE-FLOW VALVE

CROSS-REFERENCE TO RELATED APPLICATIONS

The present application is the US national stage application of PCT/IL2020/050249, filed Mar. 4, 2020, which published as PCT Publication WO 2020/178827 to Shoham, and which claims the priority of U.S. 62/814,053 to Shoham, filed Mar. 5, 2019 entitled, "Anti-free-flow valve," which is incorporated herein by reference.

FIELD OF THE INVENTION

The present invention relates generally to medical fluid-delivery devices, and more specifically to infusion pumps.

BACKGROUND

Pumps are often used in the medical industry for delivering fluids, e.g., drugs or diagnostic fluids, to subjects. One type of medical pump is an infusion pump, used to infuse a fluid into a subject's circulatory system via infusion tubing. Some infusion pumps include a valve, or system of valves, that may occlude flow within the infusion tubing by pressing on the outside of the fluid-filled infusion tubing. Often infusion pumps engage with the infusion tubing via tube cassette. A common safety feature of tube cassettes is an anti-free-flow valve that ensures that the infusion tubing is occluded in the event that the tube cassette is disengaged from the pump.

SUMMARY OF THE INVENTION

A tube cassette and infusion pump for delivering a fluid to a subject are provided, in accordance with some applications of the present invention. The tube cassette receives the infusion tubing and is removably couplable to the pump. The tube cassette comprises an anti-free-flow valve that occludes the infusion tubing and can be actuated by a force external to the tube cassette to terminate the occlusion. Thus, in the absence of the external force, i.e., in its rest-state, the anti-free-flow valve occludes the infusion tubing. The infusion pump, e.g., a volumetric infusion pump, or peristaltic infusion pump, delivers the fluid to the subject by repeatedly (a) pressing on the infusion tubing with a pressing surface so as to push fluid toward the subject and then (b) raising the pressing surface from pressing on the infusion tubing so as to intake more fluid from a fluid source. When the tube cassette is coupled to the pump, as part of a pumping cycle for delivering the fluid to the subject, the pump repeatedly (a) actuates the anti-free-flow valve to terminate the occlusion of the infusion tubing, and subsequently (b) releases the anti-free-flow valve, allowing it to return to its rest state and occlude the infusion tubing. Thus, the pump uses the anti-free-flow valve of the tube cassette to deliver the fluid from the fluid source to the subject.

For some applications, the tube cassette comprises a lever, the anti-free-flow valve being disposed on the load arm (further described hereinbelow) of the lever. The lever is spring-loaded so as to maintain the anti-free-flow valve occluding the infusion tubing. The anti-free-flow valve may be actuated to terminate the occlusion by a force applied to the effort arm (further described hereinbelow) of the lever, in opposition to the spring loading of the lever. The anti-free-flow valve may be manually actuated to terminate the occlusion by a user when the tube cassette is not coupled to the pump, e.g., by the user pressing on the effort arm of the lever in opposition of the spring loading. Additionally, the anti-free-flow valve may be actuated to terminate the occlusion by a force applied by the pump to the effort arm of the lever in opposition of the spring loading.

There is therefore provided, in accordance with some applications of the present invention, apparatus for delivering a fluid to a subject through infusion tubing, the apparatus including:

(A) a tube cassette configured to receive the infusion tubing and including an anti-free-flow valve configured to:
  (i) occlude the infusion tubing, and
  (ii) be actuated by a force external to the tube cassette to terminate the occlusion of the infusion tubing; and
(B) a pump:
  (i) the tube cassette being configured to be removably coupled to the pump, and
  (ii) the pump being configured to, as part of a pumping cycle for delivering the fluid to the subject, repeatedly (a) actuate the anti-free-flow valve to terminate the occlusion of the infusion tubing, and subsequently (b) release the anti-free-flow valve to occlude the infusion tubing.

For some applications, the pump includes a pressing surface configured to press on the infusion tubing when the tube cassette is coupled to the pump.

For some applications, the anti-free-flow valve is configured to occlude the infusion tubing in the absence of any force external to the tube cassette being applied to the anti-free-flow valve.

For some applications, the anti-free-flow valve is configured to be actuated by the subject to terminate the occlusion of the infusion tubing when the tube-cassette is not coupled to the pump.

For some applications, a length of the tube cassette is 2-20 cm.

For some applications, the pump includes at least one pump-valve disposed within the pump and configured to occlude the infusion tubing when the tube cassette is coupled to the pump.

For some applications, the at least one pump-valve is exactly one pump-valve, and is the only valve disposed within the pump when the tube cassette is not coupled to the pump.

For some applications:
  (a) the pump includes a pressing surface configured to press on the infusion tubing when the tube cassette is coupled to the pump, the anti-free-flow valve being positioned to occlude the infusion tubing on a first side of the pressing surface when the tube cassette is coupled to the pump, and
  (b) the pump-valve being positioned to occlude the infusion tubing on a second side, opposite the first side, of the pressing surface when the tube cassette is coupled to the pump.

For some applications, the pump is configured to deliver the fluid to the subject by repeatedly, sequentially:
  (a) opening an upstream valve selected from the group consisting of: the pump-valve and the anti-free-flow valve,
  (b) intaking the fluid from a fluid source by raising the pressing surface from pressing on the infusion tubing,
  (c) closing the upstream valve so as to occlude the infusion tubing upstream of the pressing surface,
  (d) terminating an occlusion of the infusion tubing that is downstream of the pressing surface by opening a downstream valve that is not the upstream valve and that is selected from the group consisting of: the pump-valve and the anti-free-flow valve, and (e) pressing on the infusion tubing using the pressing surface.

For some applications, the anti-free-flow valve is configured to be actuated to terminate the occlusion of the infusion tubing, upon the force external to the tube cassette being applied at a location along the infusion tubing longitudinally displaced from a site where the anti-free-flow valve occludes the infusion tubing.

For some applications, the tube cassette further includes a lever, the anti-free-flow valve being (a) disposed on the load arm of the lever, the lever being spring-loaded so as to maintain the anti-free-flow valve occluding the infusion tubing, and (b) configured to be actuated to terminate the occlusion of the infusion tubing by the force external to the tube cassette being applied to the effort arm of the lever, in opposition to the spring loading.

For some applications, the anti-free-flow valve is configured to be actuated to terminate the occlusion of the infusion tubing by the external force having any of a range of values, the range of values including 50 N.

For some applications, the range of values includes 25 N.
For some applications, the range of values includes 1 N.
For some applications, the range of values includes 0.5 N.

There is further provided, in accordance with some applications of the present invention, apparatus for delivering a fluid to a subject through infusion tubing, the apparatus including:
a volumetric infusion pump including:
two valves each configured to occlude the infusion tubing and one of the two valves being an anti-free-flow valve, and
a plunger configured to press on the infusion tubing between the two valves.

There is further provided, in accordance with some applications of the present invention, apparatus for use with a pump and infusion tubing, the apparatus including:
a tube cassette
(A) configured to (i) receive infusion tubing and (ii) be removably coupled to a pump, and
(B) including (i) an anti-free-flow valve and (ii) a lever, the anti-free-flow valve being:
(a) disposed on the load arm of the lever, the lever being spring-loaded so as to maintain the anti-free-flow valve occluding the infusion tubing when the infusion tubing is received within the tube cassette,
(b) configured to, when the tube cassette is not coupled to the pump, be manually actuated by a force applied to the effort arm of the lever, in opposition to the spring loading of the lever, to terminate the occlusion of the infusion tubing, and
(c) configured to, when the tube cassette is coupled to the pump, repeatedly (i) be actuated by a force applied by the pump to the effort arm of the lever, in opposition to the spring loading of the lever, to terminate the occlusion of the infusion tubing, and subsequently (ii) occlude the infusion tubing upon removal of the force.

For some applications, the anti-free-flow valve is configured to be actuated to terminate the occlusion of the infusion tubing by the force, applied manually or by the pump, having any of a range of values, the range of values including 50 N.

For some applications, the range of values includes 25 N.
For some applications, the range of values includes 1 N.
For some applications, the range of values includes 0.5 N.

The present invention will be more fully understood from the following detailed description of applications thereof, taken together with the drawings, in which:

DETAILED DESCRIPTION

Figure 1:
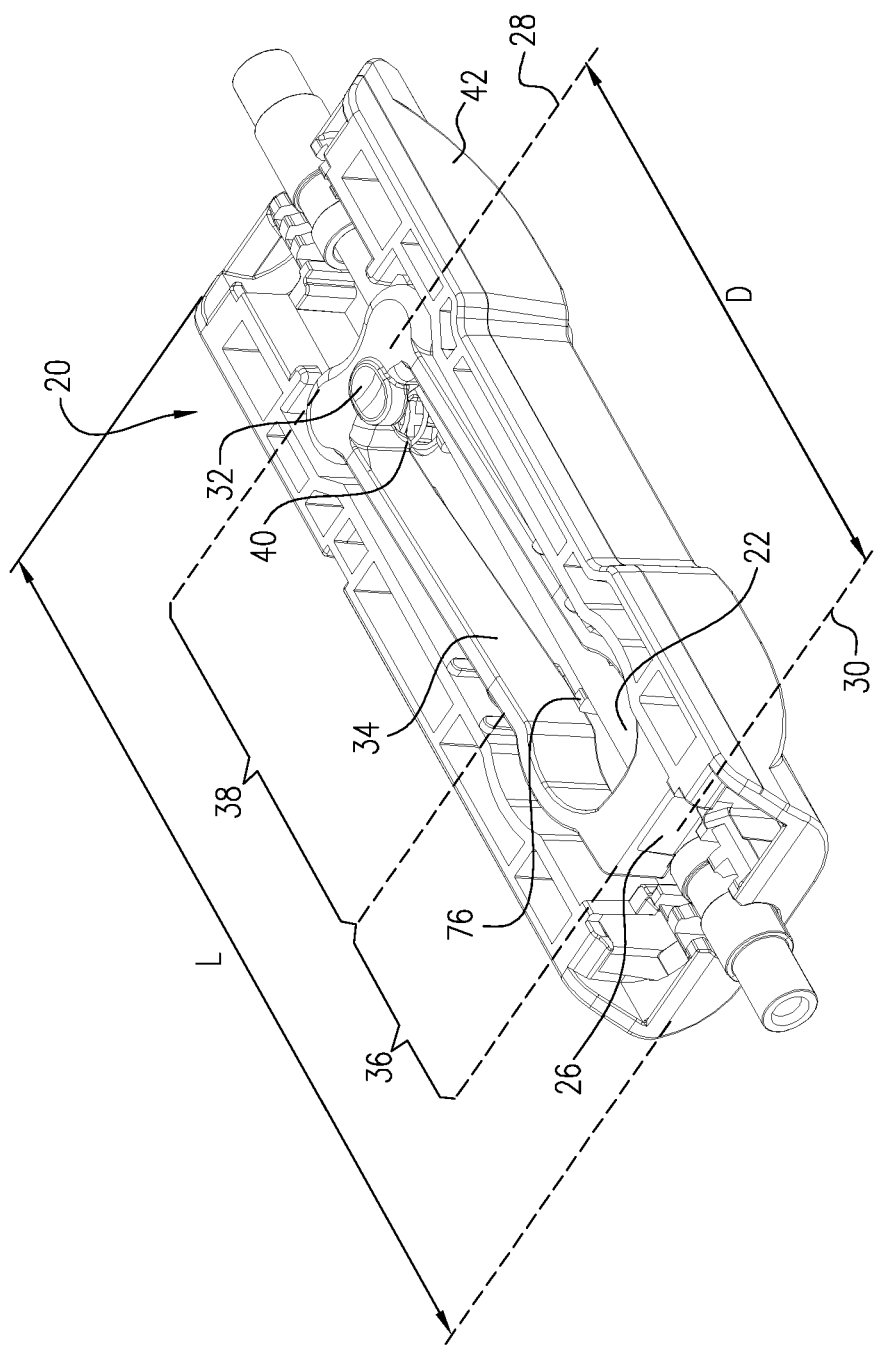
FIG. 1 is a schematic illustration of a tube cassette that is removably couplable to a pump, in accordance with some applications of the present invention.

Reference is now made to FIG. 1, which is a schematic illustration of a tube cassette 20, in accordance with some applications of the present invention. Tube cassette 20 receives infusion tubing 22 and is removably couplable to a pump 24 (shown in FIGS. 2A-B, 3A-B, and 4A-F), such that pump 24 engages with infusion tubing 22 via tube cassette 20. Tube cassette 20 comprises an anti-free-flow valve 26 that occludes infusion tubing 22 and can be actuated by a force external to tube cassette 20 to terminate the occlusion of infusion tubing 22. Thus, in the absence of any force external to tube cassette 20 being applied to anti-free-flow valve 26, i.e., anti-free-flow valve 26 is in a rest-state, anti-free-flow valve 26 occludes infusion tubing 22. Typically, when tube cassette 20 is not coupled to pump 24, such as is shown in FIG. 1, anti-free-flow valve 26 may be manually actuated by the subject to terminate the occlusion of infusion tubing 22, as is further described hereinbelow.

Typically, anti-free-flow valve 26 is actuated to terminate the occlusion of infusion tubing 22 upon the external force being applied at a location along the infusion tubing, represented by dashed line 28, that is longitudinally displaced from a site where anti-free-flow valve 26 occludes infusion tubing 22, represented by dashed line 30. For some applications, the longitudinal displacement of where the force is applied, e.g., of pressable actuator 32, from where the infusion tubing is occluded may be a distance D of at least 10 mm and/or less than 150 mm. Typically, tube cassette 20 comprises a pressable actuator 32 to which the external force used to actuate anti-free-flow valve 26 is applied. For example, when not coupled to pump 24, the subject may press on pressable actuator 32 in order to actuate anti-free-flow valve 26 to terminate the occlusion of infusion tubing 22.

For some applications, the longitudinal displacement of where the external force is applied, e.g., of pressable actuator 32, from the site where anti-free-flow valve 26 occludes infusion tubing 22, is achieved by tube cassette 20 comprising a lever 34. As is known in the field of mechanics, a first-class lever has a load arm and an effort arm positioned on either side of a fulcrum. Anti-free-flow valve 26 is disposed on, e.g., at the end of, a load arm 36 of lever 34 and pressable actuator 32 is disposed on, e.g., at the end of, an effort arm 38 of lever 34. A fulcrum 76 is disposed between load arm 36 and effort arm 38. Lever 34 is spring loaded, e.g., by a spring 40 positioned between a housing 42 of tube cassette 20 and pressable actuator 32, so as to maintain anti-free-flow valve 26 occluding infusion tubing 22. Anti-free-flow valve 26 is actuated to terminate the occlusion of infusion tubing 22 by the force external to tube cassette 20 being applied to effort arm 38 of lever 34, e.g., to pressable actuator 32 at the end of effort arm 38, in opposition to the spring loading.

Using a lever to displace (a) where the force is applied to actuate anti-free-flow valve 26 from (b) where the occlusion of infusion tubing 22 occurs, enables anti-free-flow valve 26 to be actuated to terminate the occlusion with relatively low force. For example, the force external to tube cassette 20 required to actuate anti-free-flow valve 26 can be as low as 1 N, e.g., 10 N, e.g., 20 N, e.g., 50 N, e.g., higher.

Figure 2A:
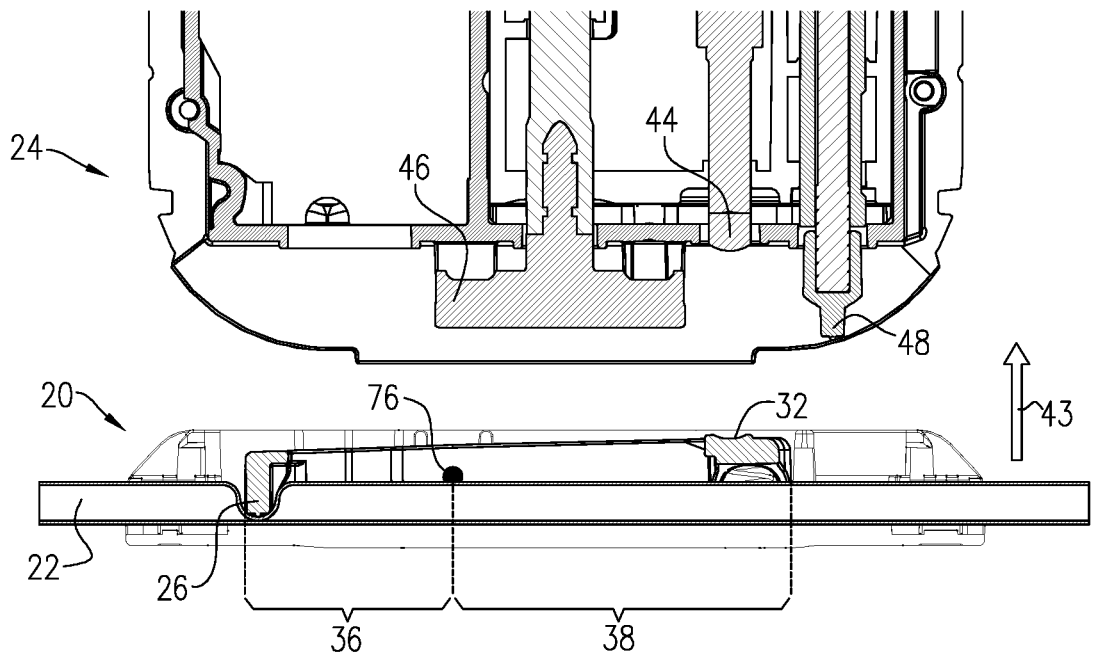
FIGS. 2A-B are schematic illustrations showing the tube cassette and the pump before and after the tube cassette has been coupled to the pump, in accordance with some applications of the present invention.
Figure 2B:
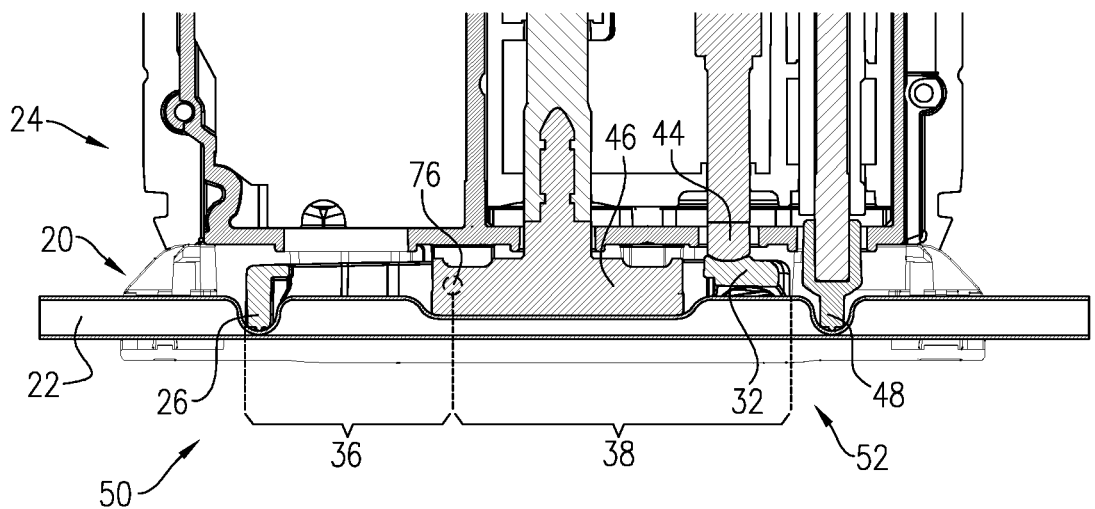

Reference is now made to FIGS. 2A-B, which are schematic illustrations showing tube cassette 20 and pump 24 before and after tube cassette 20 has been coupled to pump 24, in accordance with some applications of the present invention. Typically, pump 24 delivers the fluid to the subject from a fluid source via infusion tubing 22 by repeatedly pressing on infusion tubing 22 with a pressing surface and then raising the pressing surface from pressing on infusion tubing 22. For example, pump 24 may be a volumetric infusion pump, or a peristaltic infusion pump. FIG. 2A shows tube cassette 20 in position to be coupled to pump 24, by being inserted into pump 24, as represented by arrow 43. Within pump 24 is an anti-free-flow-valve-actuator 44 that is positioned to press on pressable actuator 32 when actuated to do so by pump 24. As part of the pumping cycle for delivering the fluid to the subject, pump 24 repeatedly (a) actuates anti-free-flow valve 26 to terminate the occlusion of infusion tubing 22, and subsequently (b) releases anti-free-flow valve 26 to occlude infusion tubing 22. That is, pump 24 uses anti-free-flow valve 26 to deliver the fluid from the fluid source to the subject.

Typically, pump 24 is a volumetric pump that delivers the fluid to the subject by controlling two valves that occlude the infusion tube on either side of a pressing surface that presses on the infusion tube (as further described hereinbelow with reference to FIGS. 4A-F). Pump 24 comprises a pressing surface 46, that presses on infusion tubing 22 and at least one, e.g., exactly one, pump-valve 48 which occludes infusion tubing 22. When tube cassette 20 is coupled to pump 24, anti-free-flow valve 26 is positioned to occlude infusion tubing 22 on a first side 50 of pressing surface 46, and pump-valve 48 is positioned to occlude infusion tubing 22 on a second side 52, opposite first side 50, of pressing surface 46. For some applications, pump-valve 48 is the only valve disposed within pump 24 when tube cassette 20 is not coupled to pump 24.

Using anti-free-flow valve 26 as a valve that is part of the delivery cycle saves space within tube cassette 20, as it is no longer necessary for tube cassette 20 to be long enough to accommodate an anti-free-flow valve, an upstream valve of the pump and a downstream valve of the pump. Rather anti-free-flow valve 26 is used as either the upstream or the downstream valve during the pumping cycle. Typically, a length L of tube cassette 20 is at least 2 cm and/or less than 20 cm.

Figure 3A:
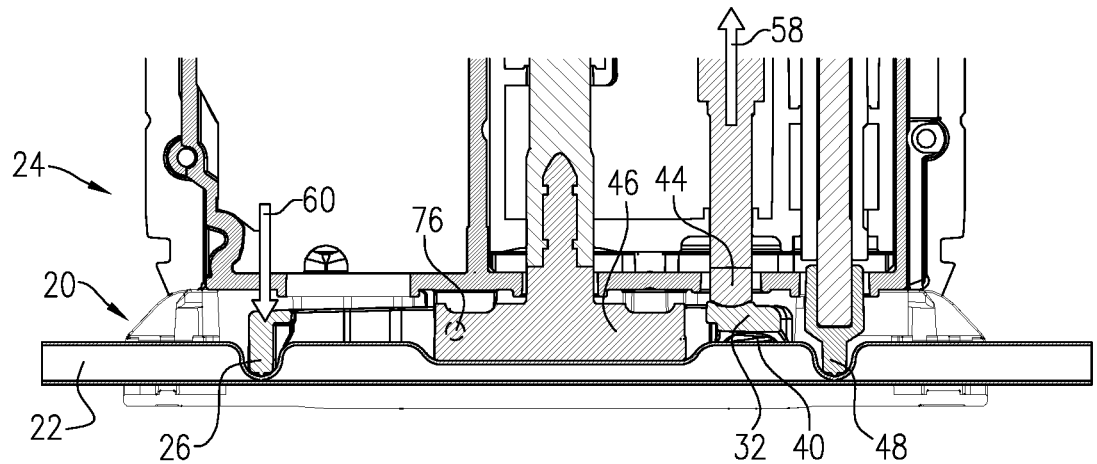
FIGS. 3A-B are schematic illustrations showing the actuation and subsequent release of the anti-free-flow valve by the pump, in accordance with some applications of the present invention.
Figure 3B:
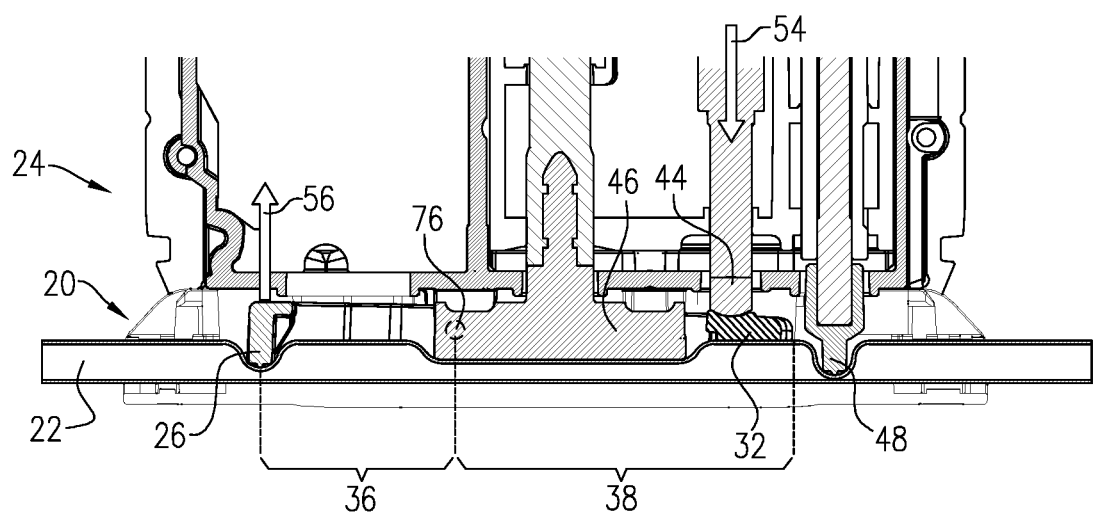

Reference is now made to FIGS. 3A-B, which are schematic illustrations depicting the actuation and subsequent release of anti-free-flow valve 26 by pump 24, in accordance with some applications of the present invention. FIG. 3A shows the positioning of pressable actuator 32 at the end of effort arm 38 of lever 34, anti-free-flow-valve-actuator 44 and anti-free-flow valve 26 when tube cassette 20 is first coupled to pump 24. To actuate anti-free-flow valve 26 to remove the occlusion of infusion tubing 22, pump 24 actuates anti-free-flow-valve-actuator 44 to press on pressable actuator 32 at the end of effort arm 38, in opposition of the spring loading, e.g., in opposition of the spring force provided by spring 40. This pressing of pressable actuator 32 is represented by downward facing arrow 54 in FIG. 3B. As a result, load arm 36 moves in an opposite direction, represented by upward arrow 56 in FIG. 3B, thereby lifting anti-free-flow valve 26 away from infusion tubing 22 to terminate the occlusion of infusion tubing 22.

When anti-free-flow-valve-actuator 44 is moved, by pump 24, in an upward direction, represented by upward arrow 58 in FIG. 3A, anti-free-flow-valve-actuator 44 no longer presses on pressable actuator 32, thereby allowing the spring loading of lever 34 to push pressable actuator 32 back up to its starting position, and in turn, anti-free-flow valve 26 back down to its occluding position, represented by downward arrow 60 in FIG. 3A.

Figure 4A:
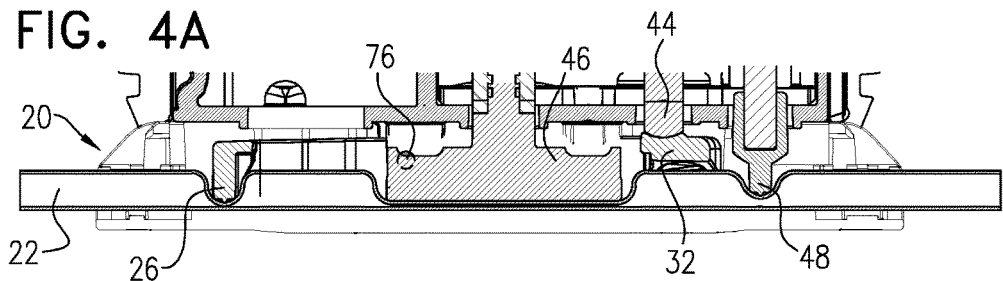
FIGS. 4A-F are schematic illustrations depicting a pumping cycle of the pump, in accordance with some applications of the present invention.
Figure 4B:
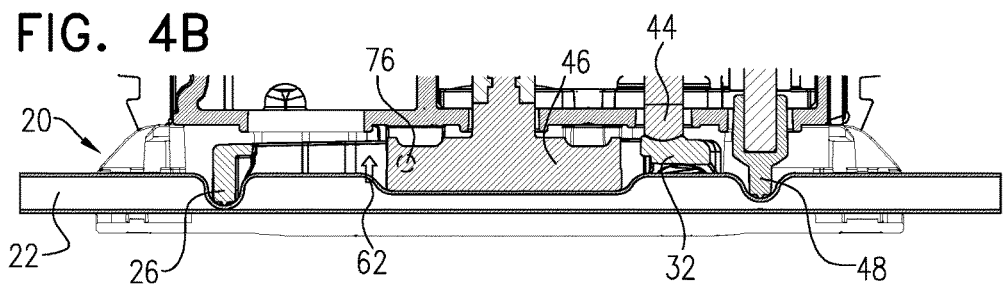
Figure 4C:
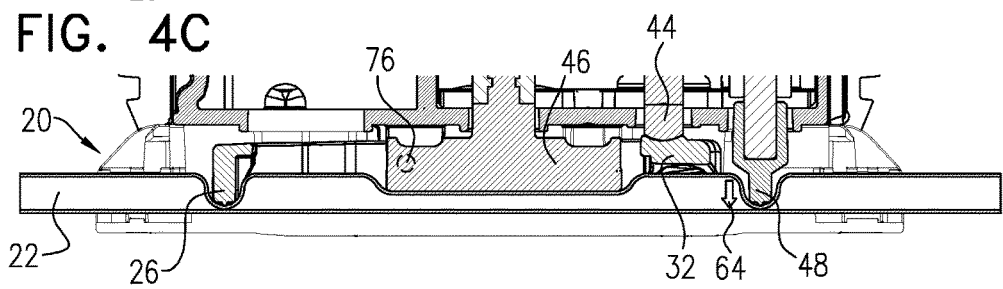

Reference is now made to FIGS. 4A-F, which are schematic illustrations depicting a pumping cycle of pump 24, in accordance with some applications of the present invention. To deliver the fluid to the subject, pump 24 repeatedly, sequentially, cycles through the different positions shown in FIGS. 4A-E. FIG. 4A shows pump 24 and tube cassette 20 in a starting position when tube cassette 20 is coupled to pump 24. Typically, pressing surface 46 starts in a position in which it is pressing down on infusion tubing 22. Pump-valve 48, which in this configuration is acting as an upstream valve, starts in an open position such that there is no occlusion of infusion tubing 22 upstream of pressing surface 46. Pump 24 intakes the fluid from a fluid source by increasing the volume of a pumping segment of infusion tubing 22 (i.e., the segment of infusion tubing 22 that is disposed between pump-valve 48 and anti-free-flow valve 26) by raising pressing surface 46 from pressing on infusion tubing 22. The raising of pressing surface 46 is represented by upward arrow 62 in FIG. 4B. Subsequently to the intake of the fluid, pump 24 closes the upstream valve, i.e., pump-valve 48, so as to occlude infusion tubing 22 upstream of pressing surface 46, as represented by downward arrow 64 in FIG. 4C.

Figure 4D:
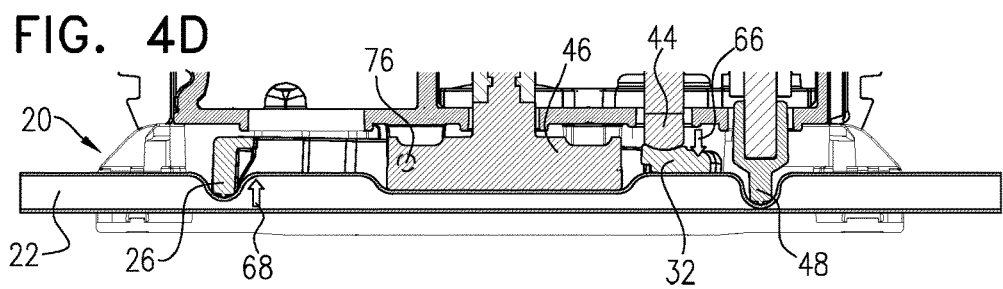

Subsequently, pump 24 actuates anti-free-flow-valve-actuator to press on pressable actuator 32, thereby terminating the occlusion of infusion tubing 22 downstream of pressing surface 46. Downward arrow 66 in FIG. 4D represents anti-free-flow-valve-actuator 44 pressing downward, and upward arrow 68 in FIG. 4D represents anti-free-flow valve 26 terminating the occlusion of infusion tubing 22 downstream of pressing surface 46.

Figure 4E:
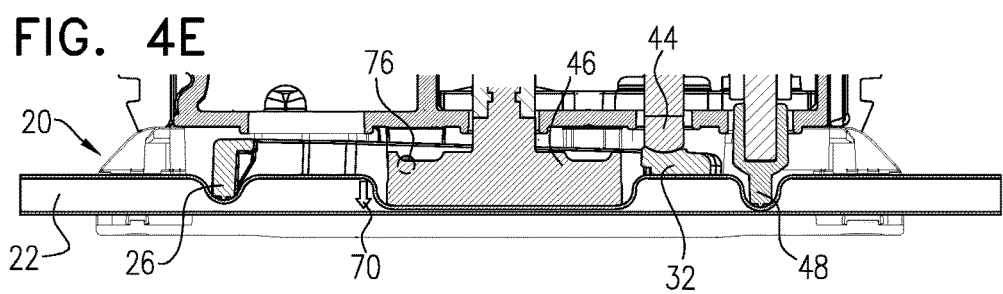
Figure 4F:
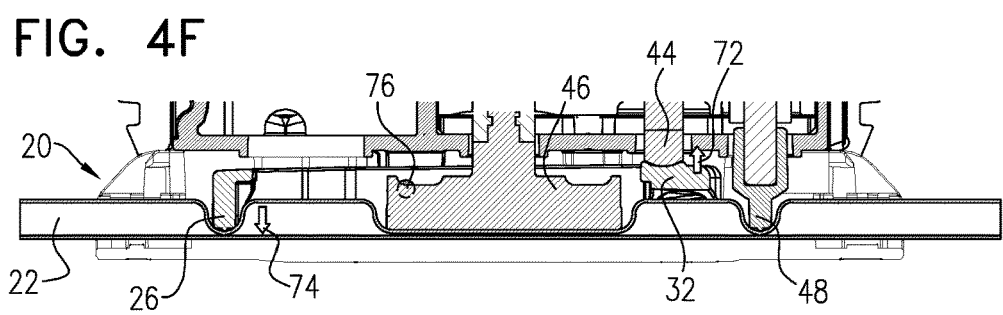

Subsequently, pump 24 actuates pressing surface 46 to press on infusion tubing 22 to push the fluid to the subject, represented by downward arrow 70 in FIG. 4E. Subsequently, anti-free-flow-valve-actuator 44 is lifted, represented by upward arrow 72 in FIG. 4F, and anti-free-flow valve 26 resumes its occlusion of infusion tubing 22, represented by downward arrow 74 in FIG. 4F. Upon the completion of the pumping cycle, the upstream valve, i.e., pump-valve 48, is opened so as to terminate the occlusion upstream of pressing surface 46, thereby returning pump 24 to the starting position of FIG. 4A (in which pressing surface 46 is pressing on infusion tubing 22 and pump-valve 48 is open), in preparation for the intake of fluid for the next pumping cycle.

It is noted that in the configuration depicted, pump-valve 48 acts as the upstream valve, and anti-free-flow valve 26 acts as the downstream valve. This, however, is non-limiting, and it is within the scope of the present invention for pump-valve 48 to be positioned as the downstream valve and anti-free-flow valve 26 to be positioned as the upstream valve when tube cassette 20 is coupled to pump 24.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for delivering a fluid to a subject through infusion tubing, the apparatus comprising:
   (A) a tube cassette configured to receive the infusion tubing and comprising an anti-free-flow valve configured to:
      (i) occlude the infusion tubing, and
      (ii) be actuated by a force external to the tube cassette to terminate the occlusion of the infusion tubing, upon the force external to the tube cassette being applied at a location along the infusion tubing longitudinally displaced from a site where the anti-free-flow valve occludes the infusion tubing; and
   (B) a pump:
      (i) the tube cassette being configured to be removably coupled to the pump, the pump comprising a pressing surface configured to press on the infusion tubing when the tube cassette is coupled to the pump, and
      (ii) the pump being configured to, as part of a pumping cycle for delivering the fluid to the subject, repeatedly (a) actuate the anti-free-flow valve to terminate the occlusion of the infusion tubing, and subsequently (b) release the anti-free-flow valve to occlude the infusion tubing,
         wherein the anti-free-flow valve is configured to occlude the infusion tubing by moving in the same direction as the direction in which the pressing surface presses on the infusion tubing.

2. The apparatus according to claim 1, wherein the anti-free-flow valve is configured to occlude the infusion tubing in an absence of any force external to the tube cassette being applied to the anti-free-flow valve.

3. The apparatus according to claim 1, wherein the anti-free-flow valve is configured to be actuated by the subject to terminate the occlusion of the infusion tubing when the tube cassette is not coupled to the pump.

4. The apparatus according to claim 1, wherein a length of the tube cassette is 2-20 cm.

5. The apparatus according to claim 1, wherein the pump comprises at least one pump-valve disposed within the pump and configured to occlude the infusion tubing when the tube cassette is coupled to the pump.

6. The apparatus according to claim 5, wherein the at least one pump-valve is exactly one pump-valve, and is the only valve disposed within the pump when the tube cassette is not coupled to the pump.

7. The apparatus according to claim 5, wherein:
   (a) the anti-free-flow valve being positioned to occlude the infusion tubing on a first side of the pressing surface when the tube cassette is coupled to the pump, and
   (b) the at least one pump-valve being positioned to occlude the infusion tubing on a second side, opposite the first side, of the pressing surface when the tube cassette is coupled to the pump.

8. The apparatus according to claim 7, wherein the pump is configured to deliver the fluid to the subject by repeatedly, sequentially:
   (a) opening an upstream valve selected from the group consisting of: the at least one pump-valve and the anti-free-flow valve,
   (b) intaking the fluid from a fluid source by raising the pressing surface from pressing on the infusion tubing,
   (c) closing the upstream valve so as to occlude the infusion tubing upstream of the pressing surface,
   (d) terminating an occlusion of the infusion tubing that is downstream of the pressing surface by opening a downstream valve that is not the upstream valve and that is selected from the group consisting of: the at least one pump-valve and the anti-free-flow valve, and
   (e) pressing on the infusion tubing using the pressing surface.

9. The apparatus according to claim 1, wherein the tube cassette further comprises a lever, the anti-free-flow valve being
   (a) disposed on the load arm of the lever, the lever being spring-loaded so as to maintain the anti-free-flow valve occluding the infusion tubing, and
   (b) configured to be actuated to terminate the occlusion of the infusion tubing by the force external to the tube cassette being applied to the effort arm of the lever, in opposition to the spring-loading.

10. The apparatus according to claim 9, wherein the anti-free-flow valve is configured to be actuated to terminate the occlusion of the infusion tubing by the force external to the tube cassette having any of a range of values, the range of values including 50 N.

11. The apparatus according to claim 10, wherein the range of values includes 25 N.

12. The apparatus according to claim 11, wherein the range of values includes 1 N.

13. The apparatus according to claim 12, wherein the range of values includes 0.5 N.

* * * * *